(12) United States Patent
Chen et al.

(10) Patent No.: US 12,129,342 B2
(45) Date of Patent: Oct. 29, 2024

(54) PRETREATMENT OF LIGNOCELLULOSE USING TWO STAGE ALKALI AND MECHANICAL REFINING PROCESSES

(71) Applicant: Alliance for Sustainable Energy, LLC, Golden, CO (US)

(72) Inventors: Xiaowen Chen, Littleton, CO (US); Michael E. Himmel, Littleton, CO (US); Richard T. Elander, Evergreen, CO (US); Melvin P. Tucker, Lakewood, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 17/976,303

(22) Filed: Oct. 28, 2022

(65) Prior Publication Data

US 2023/0145233 A1 May 11, 2023

Related U.S. Application Data

(60) Provisional application No. 63/273,804, filed on Oct. 29, 2021.

(51) Int. Cl.
*C12P 7/06* (2006.01)
*C08H 8/00* (2010.01)
*C12P 7/10* (2006.01)

(52) U.S. Cl.
CPC . *C08H 8/00* (2013.01); *C12P 7/10* (2013.01)

(58) Field of Classification Search
CPC .......... Y02E 50/10; D21C 1/06; D21C 5/005; D21C 9/02; D21C 9/18; D21C 1/02
USPC ................................................. 435/161, 162
See application file for complete search history.

(56) References Cited

U.S. PATENT DOCUMENTS

| | | |
|---|---|---|
| 10,695,747 B2 | 6/2020 | Shibata et al. |
| 10,730,958 B2 | 8/2020 | Balan et al. |
| 10,899,894 B2 | 1/2021 | Olsson et al. |
| 10,954,316 B2 | 3/2021 | Harris et al. |
| 11,066,526 B2 | 7/2021 | Jing Jing et al. |
| 11,097,251 B2 | 8/2021 | Shibata et al. |
| 11,198,765 B2 | 12/2021 | Olsson et al. |
| 11,254,792 B2 | 2/2022 | Olsson et al. |
| 11,420,992 B2 | 8/2022 | Nguyen et al. |
| 11,440,999 B2 | 9/2022 | Balan et al. |
| 11,530,301 B2 | 12/2022 | Mojarradi et al. |
| 2005/0241073 A1 | 11/2005 | Smith et al. |
| 2011/0207177 A1 | 8/2011 | Sugiura et al. |
| 2013/0274455 A1 | 10/2013 | Parekh et al. |
| 2014/0377812 A1 | 12/2014 | Louret et al. |
| 2021/0108036 A1 | 4/2021 | Olsson et al. |
| 2022/0169804 A1 | 6/2022 | Olsson et al. |
| 2022/0177655 A1 | 6/2022 | Olsson et al. |

FOREIGN PATENT DOCUMENTS

| | | |
|---|---|---|
| WO | 2011/059376 A1 | 5/2011 |
| WO | 2018/069499 A1 | 4/2018 |
| WO | 2020/152178 A1 | 7/2020 |
| WO | 2021/230274 A1 | 11/2021 |

OTHER PUBLICATIONS

Bertaud et al., "Ozonation of a β-0-4 Dimer Lignin Model: By-Product identification and Reaction Pathways", Ozone: Science & Engineering, 2001, vol. 23, No. 2, pp. 139-148.
Chen et al., "Microbial electrochemical treatment of biorefinery black liquor and resource recovery", Green Chemistry, 2019, vol. 21, No. 6, pp. 1258-1266.
Chen et al., "Kinetics and Rheological Behavior of Higher Solid (Solids >20%) Enzymatic Hydrolysis Reactions UsingDilute Acid Pretreated, Deacetylation and Disk Refined, and Deacetylation and Mechanical Refined (DMR) Com StoverSlurries", ACS Sustainable Chemistry & Engineering, 2019, vol. 7, No. 1, pp. 1633-1644.
Cronin et al., "Deep Eutectic Solvent Extraction of High-Purity Lignin from a Corn Stover Hydrolysate", ChemSusChem, 2020, vol. 13, No. 17, pp. 4678-4690.
Corma et al., "Hydrogenation of aromatics in diesel fuels on Pt/MCM-41 catalysts", Journal of Catalysis, 1997, vol. 169, No. 2, pp. 480-489.
Davis et al., "Process Design and Economics for the Conversion of Lignocellulosic Biomass to Hydrocarbon Fuels and Products: 2018 Biochemical Design Case Update", NREL Technical Report NREL/TP-5100-71949, Nov. 2018, pp. 1-147.
Dimmel et al., "Pulping Catalysts from Lignin: The Diels-Alder Step", Institute of Paper Science and Technology Atlanta, Georgia, IPST Technical Paper Series No. 913, Jul. 2001, pp. 1-28.
Fray et al., "Catalysis of the Diels-Alder reaction", Journal of the American Chemical Society, 1961, vol. 83, No. 1, pp. 249-249.
Hendrickson et al., "Catalysis and regioselectivity of quinone Diels-Alder reactions", Journal of the Chemical Society, Chemical Communications 1983, vol. 15, pp. 837-838.
Kuhn et al., "Deacetylation and Mechanical Refining (DMR) and Deacetylation and Dilute Acid (DDA)Pretreatment of Corn Stover, Switchgrass, and a 50:50 Corn Stover/Switchgrass Blend", 2020, ACS Sustainable Chemistry &Engineering, vol. 8, No. 17, pp. 6734-6743.
Pehnt, "Dynamic life cycle assessment (LCA) of renewable energy technologies", Renewable Energy, Jan. 2006, vol. 31, No. 1, pp. 55-71.

(Continued)

*Primary Examiner* — Robert B Mondesi
*Assistant Examiner* — Mohammad Y Meah
(74) *Attorney, Agent, or Firm* — Sam J. Barkley

(57) ABSTRACT

Disclosed herein are processes for ethanol production from a lignocellulosic feedstock. These processes provide DMR of lignocellulosic biomass comprising two-stage deacetylation followed by mechanical refining so as to increase fermentable sugar yield while reducing hydrolytic enzyme loading requirements.

8 Claims, 8 Drawing Sheets

(56) References Cited

OTHER PUBLICATIONS

Saa et al., "Oxidative degradation approach to p-quinones", The Journal of Organic Chemistry, 1986, vol. 51, No. 23, pp. 4471-4473.
Tou et al., "Selective catalysis of Diels-Alder reactions of 2-methoxy-5-methyl-1, 4-benzoquinone", The Journal of Organic Chemistry, 1980, vol. 45, No. 24, pp. 5012-5014.
Wang et al., "Characterization and Deconstruction of Oligosaccharides in Black Liquor From Deacetylation Process of Corn Stover", 2019, Frontiers in Energy Research, vol. 7, No. 54, pp. 1-10.
Wozniak et al., "The Generation of Quinones from Lignin and Lignin-Related Compounds", Journal of Wood Chemistry and Technology, 1989, vol. 9, No. 4, pp. 491-511.
Yates et al., "Acceleration of the Diels-Alder reaction by aluminum chloride", Journal of the American Chemical Society, 1960, vol. 82 No. 16, pp. 4436-4437.
International Search Report and Written Opinion for International (PCT) Application No. PCT/US2022/048212, mail date Mar. 6, 2023, pp. 1-11.

PRETREATMENT OF LIGNOCELLULOSE USING TWO STAGE ALKALI AND MECHANICAL REFINING PROCESSES

CROSS-REFERENCE TO RELATED APPLICATIONS

This application claims priority to U.S. Provisional Patent Application No. 63/273,804 filed on Oct. 29, 2021, and entitled "CARBON NEUTRAL PRETREATMENT OF LIGNOCELLULOSE USING TWO STAGE ALKALI AND MECHANICAL REFINING PROCESSES," the entire contents of which are hereby incorporated herein by reference.

GOVERNMENTAL SUPPORT

This invention was made with government support under Contract No. DE-AC36-08GO28308 awarded by the Department of Energy. The government has certain rights in the invention.

BACKGROUND

In the field of ethanol production from lignocellulosic feedstocks, there is a need for approaches to improving the effectiveness of deacetylation and mechanical refining (DMR) processes while reducing materials requirements and greenhouse gas (GHG) emissions.

Objects, advantages, and novel features of the present invention will become apparent from the following detailed description of the invention when considered in conjunction with the accompanying drawings.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
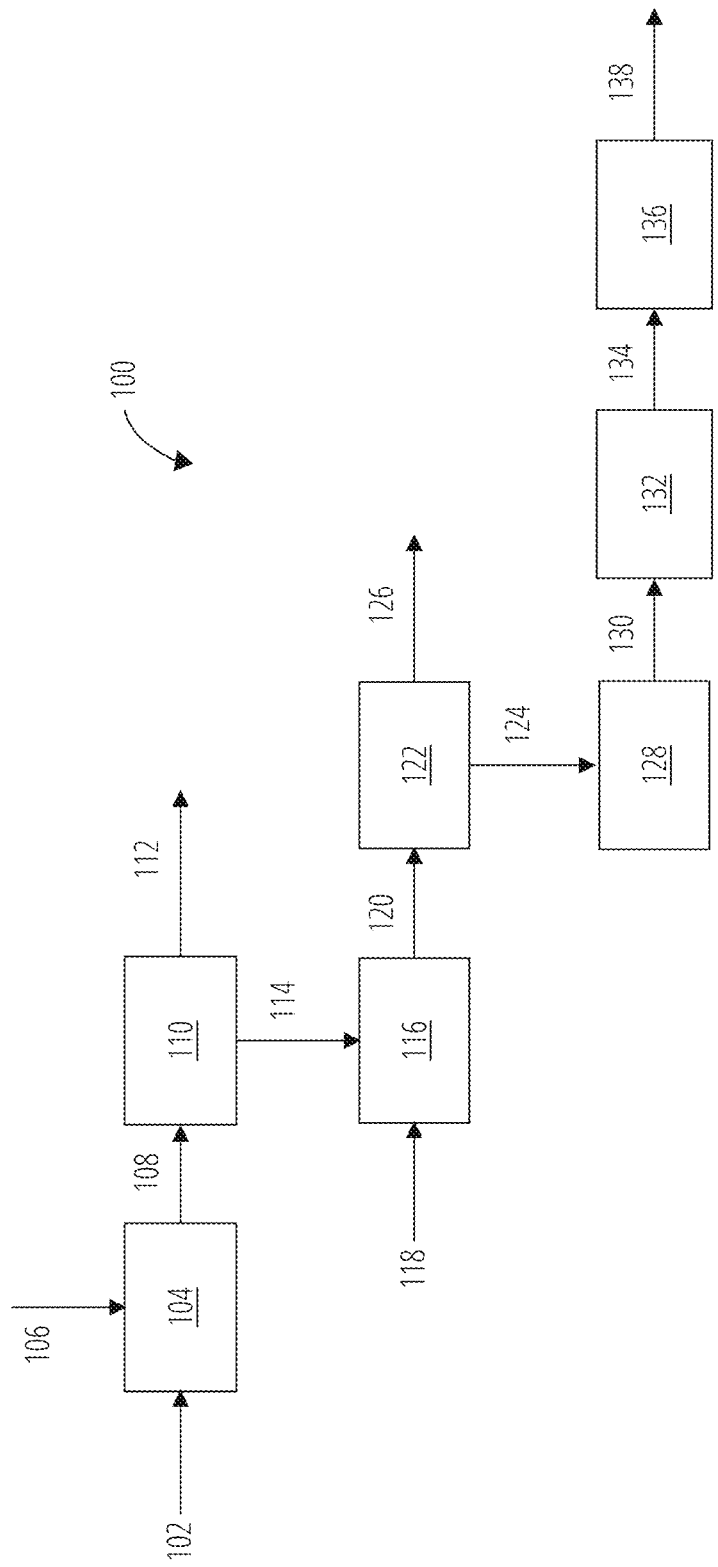
FIG. 1 depicts a diagram of an embodiment of the processes disclosed herein.

Methods and systems disclosed herein provide a DMR process for pretreating lignocellulosic biomass so as to increase fermentable sugar yield, while reducing inhibitor production and hydrolytic enzyme loading requirements. The DMR process not only increases sugar yields/titers/fermentabilities relative to existing pretreatments, but also decreases operational costs, including chemical and energy costs. The inventors have found that dilute alkali deacetylation at very mild conditions saponifies acetyl groups from the xylan backbone of lignocellulosic biomass, which not only increases the fermentability of the sugar stream that is produced (particularly if acetic acid is carried away in the deacetylation black liquor) but also reduces the recalcitrance of the biomass. Methods disclosed herein may be implemented to achieve very high (≥80%) monomeric sugar yields from hydrolysis of DMR solids at low hydrolytic protein loading. In an embodiment, the hydrolytic enzyme loading is from about 10 to 30 mg enzyme per gram cellulose content in the biomass feedstock.

In the processes disclosed herein, DMR comprises two-stage deacetylation followed by mechanical refining. In some embodiments, the solvents used in the two-stage deacetylation are one or more theta solvents for lignin, such as alkaline solvents. Alkali may be referred to as a pseudo-theta solvent for plant cell wall lignin. In a theta solvent, dissolved polymers retain most of their native configuration (size and shape), are not chemically modified, and are fully solvated. In contrast, acid pretreatments break bonds in sugars and cause lignin to self-sequester, forming small, hydrophobic micelles or droplets which remain in the hot solution. Upon cool down or neutralization, these droplets recondense or plate back onto the cellulose surfaces. This results in much higher loadings of expensive cellulase enzymes to achieve the same percent conversion to sugars compared to an alkaline process. Organic solvent pretreatment, also called organosolv, performs a similar function in solubilizing and removing lignin; however, these solvents are very costly and pose a hazardous working environment for the factory operators. Hazards include explosion, cancer, and teratogenesis. Most process engineers do not prefer organosolv based pretreatments for these reasons.

In some embodiments, the solvents used in the two-stage deacetylation comprise a first alkali used in a first stage followed by a second alkali used in a second stage. In some embodiments, the first alkali is a weak alkali and the second alkali is a strong alkali. "Weak alkali" and "strong alkali" are defined here as bases able to produce in aqueous solution pH values of pH 10 to pH 12 and pH 12 and higher, respectively, at concentrations of 0.01 M to 0.1 M.

In an embodiment, the first alkali and the second alkali have substantially the same pH. In an embodiment, the pH is from about 10 to about 12. In another embodiment, the second alkali is the same as the first alkali. In an embodiment, the first alkali and the second alkali comprise sodium carbonate. In another embodiment, contacting with the second alkali comprises at least one of a higher temperature, a longer residence time, and a higher alkali concentration as compared to contacting with the first alkali.

A flow for a DMR process 100 according to an embodiment is depicted in FIG. 1. The feedstock 102 for the process can comprise lignocellulosic biomass such as corn stover, and anatomical fractions thereof, sorghum stover and anatomical fractions thereof, rice straw, wheat straw, cotton residue, sunflower straw, sugarcane bagasse, rice hulls, *Miscanthus giganteus*, switch grass, duckweed, kudzu, and perennial vines. The feedstock 102 may be prepared for use in the process, for example the feedstock 102 may be milled to obtain a particular particle size distribution profile. In an embodiment, the feedstock is milled to particles having an average diameter of one-quarter of an inch to two inches. In an embodiment, the feedstock is milled to particles having an average diameter of one-half of an inch to one inch. In an embodiment, the feedstock can comprise corn stover milled to one half to three quarters inch particles.

A first deacetylation stage 104 can comprise combining the feedstock 102 with an amount of a first stage extraction solvent 106. In an embodiment, the first stage extraction solvent 106 comprises a first alkali. The first alkali results in an extraction and may be a weak alkali, i.e., producing an aqueous pH of about 10 to about 12. Alkalis that may be used in this stage include sodium carbonate, potassium carbonate, ammonium hydroxide, magnesium hydroxide, trimethylamine, or methylamine. In a particular embodiment, the first stage extraction solvent 106 comprises sodium carbonate. The amount of first alkali in the first stage extraction solvent 106 can be from about 40 kg to about 100 kg per tonne of biomass. In more particular embodiments, the amount of first alkali can be about 40 kg to about 70 kg, about 50 kg to about 90 kg, about 60 kg to about 80 kg, about 60 kg to about 90 kg, or about 70 kg to about 100 kg, each of the foregoing being per tonne of biomass. In an embodiment, a horizontal paddle type high solids blender or reactor may be used in the methods disclosed herein. In an embodiment, biomass particles from about 5% to 35% wt/wt range may be used in methods disclosed herein.

In some embodiments, ammonium hydroxide in the form of liquid ammonia (3 to 6 grams per liter of biomass slurry, for example) can be used as an extraction solvent in the first deacetylation stage 104. In such embodiments, the solvent may be removed from the biomass slurry before subsequent process stages to avoid reversion of the liquid ammonia to its more toxic gaseous state.

After the first deacetylation stage 104, the first stage biomass 108 can then undergo dewatering 110 to produce two output streams: a first stage black liquor 112 and a first stage solids 114. In an embodiment, a screw type solid-liquid separator (such as an Andritz Impressafiner™) can be used for this step. Other solid-liquid separation equipment suitable for the biomass may be used. In some embodiments, dewatering 110 may comprise one or more cycles of rinsing and dewatering. The first deacetylation stage 104 removes most of the ash content in biomass (which is significant in cereal grasses and maize family plants where it can be as high as 10% wt/wt) as well as removing acetate, xylooligomers and most of the soluble low MW phenolics. In an embodiment, the first dewatering step of the DMR process as depicted in FIG. 1 results in a first stage black liquor 112 having removed 60-90% acetate and 60-90% ash concentration, 5-15% lignin concentration, and <5% xylooligomers; as well as from about 3 to about 30 wt % solids.

The first stage solids 114 then undergo a second deacetylation stage 116 comprising combining the first stage solids 114 with a second stage extraction solvent 118 comprising an amount of a second alkali. In some embodiments the second alkali produces an extraction pH that is higher than that of the first alkali. The second alkali may be a strong alkali, i.e., having a pH equal to or greater than about pH 12, e.g., pH 12 to 13. Alkalis that may be used include sodium hydroxide, potassium hydroxide, barium hydroxide, calcium hydroxide, trisodium phosphate, and tripotassium phosphate. In an embodiment, the strong alkali is sodium hydroxide. The amount of second alkali in the second stage extraction solvent 118 can be from about 10 kg to about 40 kg per tonne of biomass. In more particular embodiments, the amount of second alkali per tonne of biomass can be about 10 kg to about 20 kg, about 20 kg to about 30 kg, about 30 kg to about 40 kg, about 25 kg to about 35 kg, or about 24 kg to about 59 kg. In some embodiments, the second alkali loading may be based at least in part upon the loading of first alkali used in the first deacetylation stage 104. For example, a first deacetylation stage 104 with a higher first alkali loading may be followed with a second deacetylation stage 116 having a lower second alkali loading, or vice versa. In some embodiments, the amount of first alkali can be about 60 kg to about 80 kg per tonne of lignocellulosic biomass and the amount of second alkali about 24 kg to about 40 kg per tonne of lignocellulosic biomass. In some embodiments, the amount of first alkali can be about 40 kg to about 60 kg per tonne of lignocellulosic biomass and the amount of second alkali about 40 kg to about 59 kg per tonne of lignocellulosic biomass. In an embodiment of the methods disclosed herein, horizontal paddle type high solids blenders or reactors rated to 10 psig may be used. In an embodiment, biomass particles from about 5% to about 35% wt/wt range may be used in methods disclosed herein.

After the second deacetylation stage 116, the deacetylated second stage biomass 120 can then undergo dewatering 122. Similar equipment may be used for this step as for dewatering 110. The second deacetylation stage 116 removes process ash and most of the lignin, which is recovered as higher molecular weight (MW) lignin than the lignin in the first stage black liquor 112. In some embodiments, the second dewatering step 122 of FIG. 1 results in an output stream of a second stage solids 124 and also an output stream of second stage black liquor 126 having lignin concentrations in the range of 3-10 g/L (30-60% of initial lignin content of biomass), 1-4 g/L of carbohydrate, and low (for example less than 20% of starting biomass) process ash. In an embodiment, the DMR process as depicted in FIG. 1 removes lignin while preserving sufficient lignocellulosic structure (lignin-carbohydrate complexes) to allow better enzyme penetration that results in higher sugars yield. In an embodiment, the DMR process as depicted in FIG. 1 removes about 5% to about 15%, or about 10%, lignin of the biomass at the stage 1 deacetylation. In an embodiment, the DMR process as depicted in FIG. 1 removes about 20% to about 50% or about 30% to about 40% lignin of biomass at the stage 2 deacetylation. The particular levels of lignin removal may depend upon the biomass used.

The DMR processes disclosed herein use two stages of alkali extractions performed under relatively mild conditions to prepare lignocellulosic biomass for hydrolytic enzyme treatment which liberates fermentable sugars. In some embodiments, one or both deacetylation stages 104, 116 are performed at hot (but usually below boiling, for example from about 80° C. up to about 100° C.) temperatures and pressures at substantially near ambient pressure (for example, from about −10% to about +10% ambient pressure) or at slight pressurization (for example, about 10% above ambient pressure). In some embodiments, ambient pressure is 101,325 pascals±30%. During this process the lignin entrained in the plant cell walls is solubilized and extracted cleanly by the second deacetylation step. This lignin fraction is substantially free from acetate and native biomass ash. Most other pretreatments do not accomplish this. In an embodiment, the 2-stage deacetylation does not lead to significantly higher carbohydrate dissolution in black liquor as compared to single-stage NaOH only deacetylation. In an embodiment, the 2-stage deacetylation is also a biomass fractionation process, which produces ash and some soluble lignin in the first black liquor and lignin with very little ash in the second black liquor fraction. These characteristics facilitate valorization of these two black liquor fractions.

The two-stage deacetylation (extraction) can be followed by one or more stages of mechanical refining 128 of the second stage solids 124. Mechanical refining uses mechanical forces (e.g., grinding) to disrupt lignocellulosic structure and reduce average particle size within the biomass. As a result, the cellulose surface area available to enzymatic action is increased, thereby increasing hydrolytic efficiency. Mechanical refining can be performed using equipment such as a single disk mill, a double disk mill, a conical plate mill, a pin mill, a ball mill, a Szego type mill, an attrition mill, an ultrasonics-assisted mill, a stone-wheel grinding mill, or a homogenizer (such as a Waring™ blender). In some embodiments, mechanical refining 128 comprises at least two successive stages, each of which may employ different equipment. In an embodiment, mechanical refining 128 comprises use of a disk refiner followed by use of a Szego-type mill. In an embodiment, multiple disk refiners are used in series, where at least two disk refiners are configured for different severities. Other mechanical refiners are also contemplated.

After mechanical refining 128, the deacetylated, refined DMR biomass 130 can undergo dewatering 132. The resulting DMR solids 134 can then undergo enzymatic hydrolysis 136, where an amount of hydrolytic and oxidative enzymes are added to the DMR solids 134 and allowed to react with cellulose to produce fermentable sugars, including glucose, xylose, and arabinose. In an embodiment, the hydrolytic and oxidative enzymes are added to the DMR solids from about 5 to about 50 mg enzymes per gram of cellulose content in the biomass stream. In an embodiment, hydrolytic enzymes used include, individually or in combination, cellulases, xylanases, amylases, debranching enzymes (e.g., xylan acetyl esterases, arabinofuranosidases, beta xylosidases), beta glucosidases, and lytic polysaccharide monooxygenases. In an embodiment, commercial lignocellulosic biomass degrading enzyme formulations may be used for enzymatic hydrolysis. As noted above, the two-stage deacetylation process removes lignin while preserving sufficient lignocellulosic structure (lignin-carbohydrate complexes) to allow better enzyme penetration that results in higher sugars yield. Accordingly, lower enzyme loadings may be used to achieve a given yield as compared to single-stage strong alkali extraction methods. In some embodiments, the amount of enzymes used in the enzymatic hydrolysis 136 is about 10 mg to about 50 mg per gram of cellulose. In some embodiments, the sugars produced by enzymatic hydrolysis 136 may be converted to ethanol, either by biological processes such as microbial fermentation, or by use of non-biological chemical catalysts. In some embodiments, the sugars may be isolated and processed to produce a powder or syrup that may be sold as a commodity or used as a chemical feedstock.

In a particular example of the DMR process 100 shown in FIG. 1, corn stover milled to one half to three quarters inch particles can be subjected in a less than 15% solids slurry to sodium carbonate pH 10-12 and then sodium hydroxide with a pH of greater than pH 12 at low temperature and atmospheric pressure (e.g., less than 100° C.) deacetylation, with intermediate draining and washing, high consistency mechanical disk refining at pH 10, and low consistency mechanical disk refining at pH 10.

By reducing NaOH and enzyme loadings, the methods described herein can reduce or alleviate the GHG emissions burden driven by the high usage of the chemicals (especially sodium), as well as reduce operational costs for the biorefinery. For example, $Na_2CO_3$ is much less expensive than NaOH. As shown in Table 1, the production of $Na_2CO_3$ is much less energy intensive compared to NaOH, consuming only ⅙ of total energy used in NaOH production and producing ⅓ of GHG emissions. In deacetylation, $Na_2CO_3$ can pre-neutralize acidic components liberated from the biomass, which may further reduce NaOH usage. In some embodiments, a $Na_2CO_3$—NaOH two-stage deacetylation followed by mechanical refining can provide equivalent enzymatic hydrolysis sugar yields and lower minimum sugar selling price (MSSP) compared to a NaOH-only deacetylation/mechanical refining process.

TABLE 1

GHG emissions of NaOH and Na₂CO₃

The Greenhouse Gases, Regulated Emissions, and Energy Use in Transportation Model (GREET)

| | GHG ($CO_2$e/kg) | Fossil Energy (MJ/kg) | Total Energy (MJ/kg) |
|---|---|---|---|
| NaOH (100%) | 2.1 | 28.9 | 32.3 |
| Na₂CO₃ (100%) | 0.7 | 5.93 | 5.94 |

Figure 2:
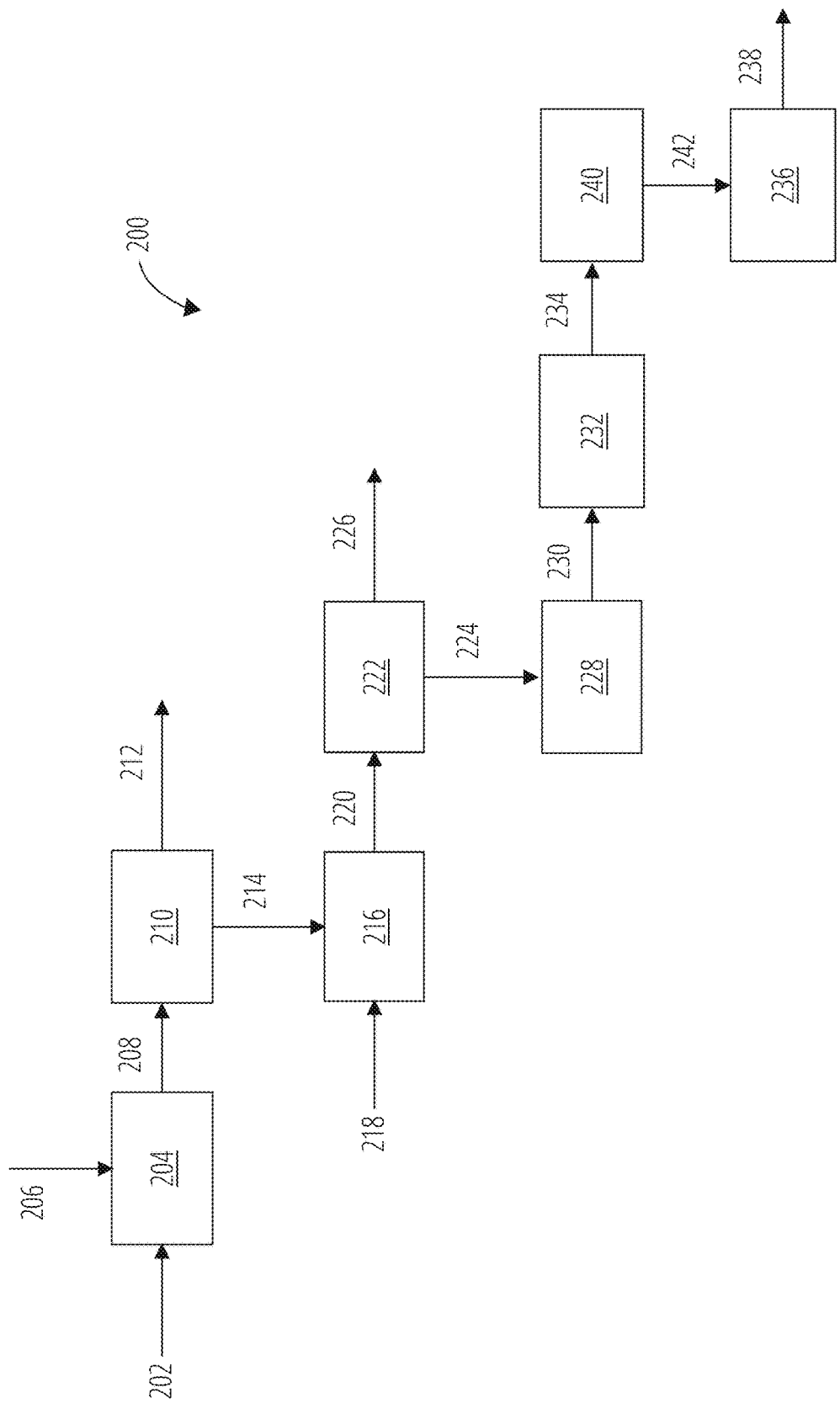
FIG. 2 depicts a diagram of another embodiment of the processes disclosed herein.

In some embodiments, ozone treatment can be combined with deacetylation and mechanical refining to further improve sugar yields and reduce the reliance on high alkali usage. Without being limited by theory, ozonolysis oxidizes the β-carbon in the propyl side chain of lignin and phenolic rings in the lignin structure, making the oxidized products much more soluble. FIG. 2 depicts an embodiment of a DMR process 200 including ozonolysis. As shown, a feedstock 202 can be subjected to a first deacetylation stage 204 with dewatering 210, the resulting first stage solids 214 subjected to a second deacetylation stage 216 with dewatering 222, followed by mechanical refining 228 of the resulting second stage solids 224, yielding a deacetylated, mechanically refined biomass 230 which is further subjected to dewatering 232 to yield DMR solids 234 substantially as described above with respect to FIG. 1. In the embodiment shown in FIG. 2, the DMR solids 234 then undergoes ozonolysis 240 before enzymatic hydrolysis 236 of the ozone treated biomass 242. However, in other embodiments, ozonolysis may be performed at other stages in the process, such as before or after one of the deacetylation stages. In some embodiments, ozonolysis may be incorporated into, or replace, one of the deacetylation stages. Ozonolysis may be performed in a reaction vessel, e.g., a pressurized vessel. In certain embodiments, ozone treatment can improve the sugar yields by up to 10%, 9%, or 8% at higher solids enzymatic hydrolysis (e.g., solids at 20% to 25%) when using low severity deacetylated corn stover. Ozone pretreatment could further remove up to 50% of lignin from deacetylated corn stover and creating new reducing ends for the cellulose fiber, resulting in higher sugar yields. In an embodiment, ozone treated DMR corn stover or other lignocellulosic biomass can be prepared with or without post-treatment washing.

However, ozone treatment could also over-pretreat high severity deacetylated and mechanical refined corn stover by over oxidizing the sugars into sugar acids, leading to reduced sugar yields. Without being bound to a particular theory, such reduction in sugar yields could be caused by the following reasons: 1) collapse of the pore structures in biomass due to the high lignin removal during ozonolysis and 2) production of enzyme inhibitors and irreversible enzyme binding sites by lignin ring-opening reactions during lignin oxidation. Accordingly, the inclusion or omission of ozone treatment in processes described herein (and the parameters of such treatment) can be selected in combination with the other stages to accomplish a targeted degree of lignin breakdown based upon the particular feedstock being used.

Black liquor streams can be processed to provide additional products. In some embodiments, one or both black liquor streams can be processed for ethanol production, particularly, the black liquor(s) may be enzymatically hydrolyzed to yield fermentable sugars, which may in turn be converted to ethanol by a biocatalytic process or by a non-biological process.

In some embodiments, the black liquor produced by the DMR process may include solubilized lignin moieties that can be upgraded for use in fuel production. For example, methods disclosed herein can be used for converting solubilized lignin monomers from the black liquor to mono- and dicyclohexane products, for example. In some embodiments, second stage black liquor 220 may be oxidized to yield one or more quinones. The quinones can then be reacted with a diene via a Diels Alder reaction to yield one or more adducts that can be hydroxydeoxygenated (HDO) to yield cyclohexanes.

EXAMPLES

Example 1. Production of Fermentable Sugars from Corn Stover Using a DMR Process A. Materials and Methods i. Feedstock Material The corn stover was knife milled (Jordan Reduction Solutions, Model 14×20, Birmingham, Alabama) to pass through a 19 mm (¾-inch) round hole rejection screen and stored indoors in 200 kg lots in super sacks. Compositional analysis of the native corn stover used in this study is shown in Table 2.

TABLE 2

Feedstock Composition

| Sample Description | % Total Ash | % Total Protein | % Lignin | % Glucan | % Xylan | % Galactan | % Arabinan | % Acetyl | Total % |
|---|---|---|---|---|---|---|---|---|---|
| Lot 15 CS | 6.97 | 2.67 | 18.16 | 36.23 | 21.34 | 1.61 | 3.25 | 2.15 | 98.26 | ii. Two-Stage Deacetylation

Two-stage deacetylation of the INL Lot #15 corn stover was carried out in a 90-L paddle type deacetylation reactor using 5.3 kg (5.0 kg dry) in a 10 wt. % slurry consisting of about 45 kg of Na₂CO₃ or NaOH at different designated loadings. The 1$^{st}$ deacetylation step was carried out using Na₂CO₃ at the prescribed loading at 90° C. for 2 h, thereafter the reactor was drained, and samples of the slurry were taken for analysis. The Na₂CO₃ deacetylated solids were then dewatered using a Vincent press (Vincent Model 10) to about 40 wt. % solids and transferred to the 90-L reactor to perform the 2$^{nd}$ deacetylation step. The target NaOH liquor loading was adjusted to achieve a final 10 wt. % solids loading in the reactor at the appropriate NaOH loading. The solids were treated again at the previous conditions for time and temperature, then dewatered, rinsed with water at 10 wt. % solids loading, then sampled and pressed using a Vincent screw press.

iii. Disk Refining

Bench-scale disk refining was carried out using a 12-inch laboratory disk refiner (Sprout Waldron Koppers model 12") equipped with type C2976 NH plates on the stationary and rotating disks. The clearance between the rotating and stationary disks was 0.01 inches (plates barely touching). The biomass was disk refined at 30% solids.

iv. Szego Milling

A Szego SM-160 mill constructed using a 160 mm inside diameter, jacketed, heavy-walled chamber, with three 60 mm diameter by 160 mm long steel rollers, was used for second stage refining. The rollers have helical grooves consisting of 5 mm ridges and 5 mm grooves with 10 mm pitch along the length of the cylindrical rollers. The deacetylated corn stover was first refined in the Sprout 12" disk refiner followed by an additional Szego milling step at a rotational speed of 1160 rpm. The biomass was refined through the Szego mill at 8% solids, then pressed to 40% solids using a Vincent press.

v. Ozonolysis

Initially, approximately 100 g of wet deacetylated/mechanically refined biomass at approximately 40% solids was loaded in a 1 L Parr reactor (Parr Instrument Company, Model 4530, Moline, IL), then the reactor lid was sealed and connected to the ozone generation system. Approximately 10% ozone in oxygen was generated by the ozone generator (Oxidation Technologies, Model 70g, Inwood, IA), at a flow rate of 1.3-1.5 L/min controlled by an ozone compatible flow meter (Ozone Solutions, Model FM-6, Hull, IA) equipped with a built-in needle valve. The ozone gas was first by-passed the reactor through simultaneous operation of the two three-way valve configuration and the ozone levels in the oxygen stream recorded by an ozone monitor (2B Technology, Model UV106-H), with data recorded through USB connections to a computer. Following baselining of the ozone concentration, the ozone gas was fed via a dip tube into the bottom of the Parr reactor by simultaneously changing the two three-way valve configurations to start the ozonolysis reactions. The residual ozone exiting the reactor was first cooled to condense the moisture produced by the ozonolysis reactions through a tube-in-shell type condenser, and then the residual ozone was measured/recorded and then was destroyed by an ozone destructor (Ozone Solutions, Model ODS-1).

vi. High Solids Enzymatic Hydrolysis

Enzymatic hydrolysis was performed in 125 mL wide-mouth polypropylene bottles (Thermo Fisher Scientific, Inc.) loaded with 30 g of neutralized slurry at 20 wt % TS (the actual solids was 22-23% accounting for the moisture loss during blending). The roller bottle saccharification reactors employ gravitational tumbling as a mixing mechanism to homogenize solids by horizontally rotating the reaction vessels containing 3×⅜" stainless steel balls at 4 rpm on a three-deck roller apparatus for mini bottles (Wheaton Industries Inc.). The roller apparatus was placed in a general-purpose incubator (Model 1545, VWR International, LLC) for temperature control at 50° C. Novozymes cellulase, Cellic CTec3, and hemicellulase, Cellic HTec3 were used at enzyme loadings of 8 mg CTec3 and 2 mg HTec3 (protein basis) per gram of cellulose. The protein concentrations of the two commercial enzyme preparations were measured by the BCA assay (Thermo Scientific Pierce Biotechnology) calibrated versus standard curves derived from bovine serum albumin (BSA) standards supplied with the kits. The enzymatic hydrolysis reactions were held for 144 hrs. Upon completion, the enzymatic hydrolysis slurries were subjected to FIS, solids compositional and liquor analyses.

vii. Gas Chromatography/Mass Spectrometry Analysis

Gas chromatography/mass spectrometry (GC-MS) analyses were performed on an Agilent 7820 gas chromatograph equipped with a HP-5 capillary column (15 m×0.25 mm i.d. and 0.25 μm film thickness) and an Agilent 5977B EI MSD detector attached. Helium was used as carrier gas (flow rate of 2 mL/min). The injector temperature was set to 280° C. The oven temperature was kept at 40° C. for 5 minutes, then increased to 250° C. at a rate of 3° C. $\text{min}^{-1}$ and held at 250° C. for 5 minutes. All samples were diluted 10-fold with acetone.

B. Results and Discussion i. Effect of 2-Stage Deacetylation on Biomass Deconstruction Table 3 shows the effect of the control and two-stage deacetylation on the dissolution of biomass components in the black liquors. The control single-stage NaOH deacetylation at 80 kg/tonne solubilized 2% glucan, 14% xylan, 42% arabinan, and 110% acetate. The results are in line with previous research showing similar sugar and acetate dissolutions during alkali extraction. The over 100% acetate yields suggests that there are small amounts of peeling reactions occurring during deacetylation that decomposes sugars into acetic acid, formic acid, and small amount dicarboxylic acids. For the two-stage deacetylation, we used three loadings of $Na_2CO_3$ for the $1^{st}$ stage deacetylation: 40, 70 and 80 kg/tonne respectively. The 40 kg $Na_2CO_3$ deacetylation dissolved 1-2.5% of glucan, 2.5-2.9% xylan, 10-20% galactan and 10-12% arabinan in all three replicates, while acetate removal is between 87-108%. The total biomass weight loss from the solids is around 16%. The results show that the 40 kg/tonne $Na_2CO_3$ loading is adequate to remove most of acetate in the biomass and results in minimal dissolution of carbohydrates. Doubling the $Na_2CO_3$ loading only leads to slightly higher carbohydrate dissolution and acetate removal.

Following the $1^{st}$ stage $Na_2CO_3$ deacetylation, different amounts of NaOH solution are added for the 2nd stage NaOH deacetylation. For the solids samples from $Na_2CO_3$ addition at 40 kg, three NaOH loadings were tested: 42, 52, and 59 kg/tonne based on the original biomass. Glucan dissolution is flat 1% for all three cases, showing the glucan loss was not affected by the increasing NaOH loadings. Xylan dissolution increased from 12% to 15% with an incremental step of approximately 1.5% when increasing the NaOH loading by 10 kg/tonne of biomass. Acetate and arabinan, however, do not show a clear trend. For the 70 and 80 kg/tonne $Na_2CO_3$ loadings, less NaOH is added to avoid over-pretreatment as we observed earlier. Accordingly, 35 and 24 kg/tonne of NaOH was added respectively, which also lead to less carbohydrate and acetate dissolution.

The highest total xylan dissolution when combining the first stage and second stage deacetylation occurs in the 40/59 case with a total xylan dissolution of 17.9%, which is about 3.5% higher than the control single stage deacetylation. The lowest xylan loss occurs in the 80/24 case with a total xylan dissolution of 12.3%. Total glucan dissolution is in the range between 2.0% to 3.5%. Total acetate removal was found between 110-160%.

TABLE 3

Effect of control and 2-stage deacetylation on biomass component dissolution in the black liquor

| Na$_2$CO$_3$ Loading (kg/tonne) | NaOH Loading (kg/tonne) | Glucan % | Xylan % | Galactan % | Arabinan % | Acetate % |
|---|---|---|---|---|---|---|
|  | 80 | 2.0% | 14.3% | 48.5% | 41.5% | 111.2% |
| 40 |  | 2.3% | 2.5% | 7.9% | 10.9% | 87.3% |
|  | 42 | 1.0% | 12.2% | 15.4% | 52.7% | 69.0% |
| 40 |  | 2.5% | 2.4% | 8.8% | 10.2% | 107.9% |
|  | 52 | 1.0% | 13.5% | 22.2% | 59.2% | 70.5% |
| 40 |  | 0.85% | 2.85% | 21.32% | 12.21% | 87.18% |
|  | 59 | 0.97% | 15.03% | 31.55% | 35.19% | 38.19% |
| 70 |  | 2.13% | 3.67% | 11.05% | 17.56% | 119.40% |
|  | 35 | 0.83% | 11.22% | 10.81% | 45.63% | 49.54% |
| 80 |  | 2.22% | 3.31% | 12.38% | 14.23% | 106.17% |
|  | 24 | 0.66% | 9.05% | 3.29% | 33.95% | 43.73% | ii. Effect of 2-Stage Deacetylation on Biomass Enzymatic Hydrolysis Yields

Figure 3:
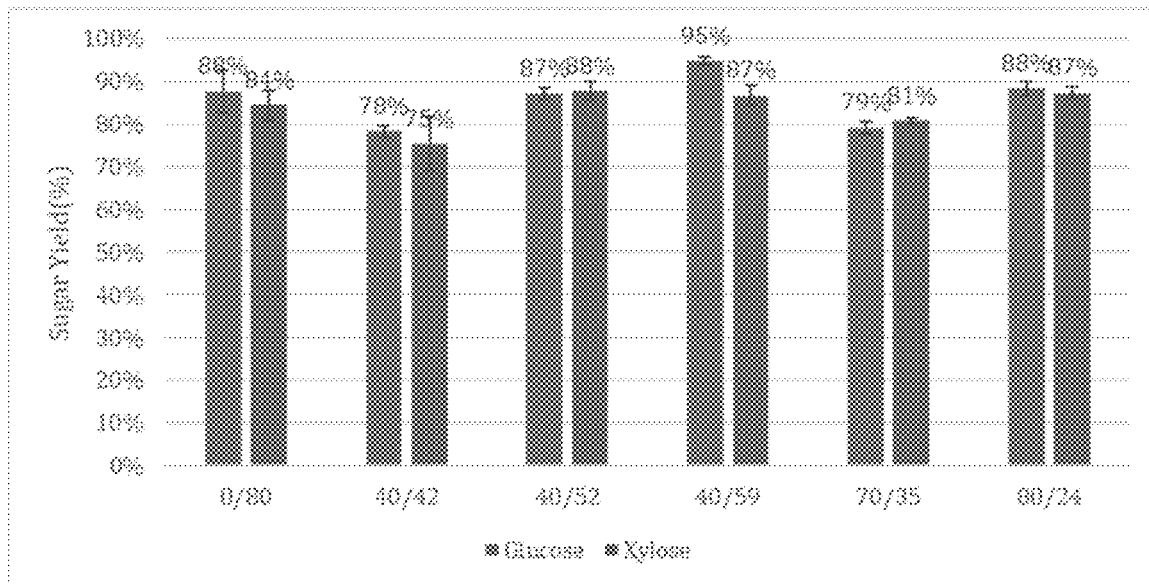
FIG. 3 depicts the effects of two-stage deacetylation severity on enzymatic hydrolysis sugar yields at 10 mg total protein (8 mg Novozymes CTec3 and 2 mg of HTec3) per gram of cellulose at 2% solids for 7 days. The numbers on the x-axis are for $Na_2CO_3$ and NaOH loadings, with the number before "/" showing $Na_2CO_3$ loadings and the number after "/" showing NaOH loadings with both units in kg/tonne, respectively. For example, "40/42" means 40 kg $Na_2CO_3$/tonne of biomass used in $1^{st}$ stage deacetylation and 42 kg NaOH/tonne of biomass used in $2^{nd}$ stage deacetylation, all based on original biomass weight.

FIG. 3 depicts the effects of the control and the two-stage deacetylation on enzymatic hydrolysis sugar yields at 10 mg total protein (8 mg CTec3 and 2 mg of HTec3 per gram of cellulose) at 2% solids for 7 days. The deacetylated biomass used was disk refined and Szego milled using similar conditions. The control batch deacetylated at 80 kg NaOH/tonne shows 88% glucose and 84% xylose yield, respectively. Three 2-stage deacetylation cases attained or almost attained an 88% yield, with the highest glucose yield achieved at 95% and xylose yield at 87% with 40 kg/tonne Na$_2$CO$_3$ in the 1$^{st}$ stage and 59 kg/tonne NaOH in the 2$^{nd}$ treatment stage. The 40/52 and 80/24 cases also showed approximately 88% glucose and 88% xylose yields.

Figure 4:
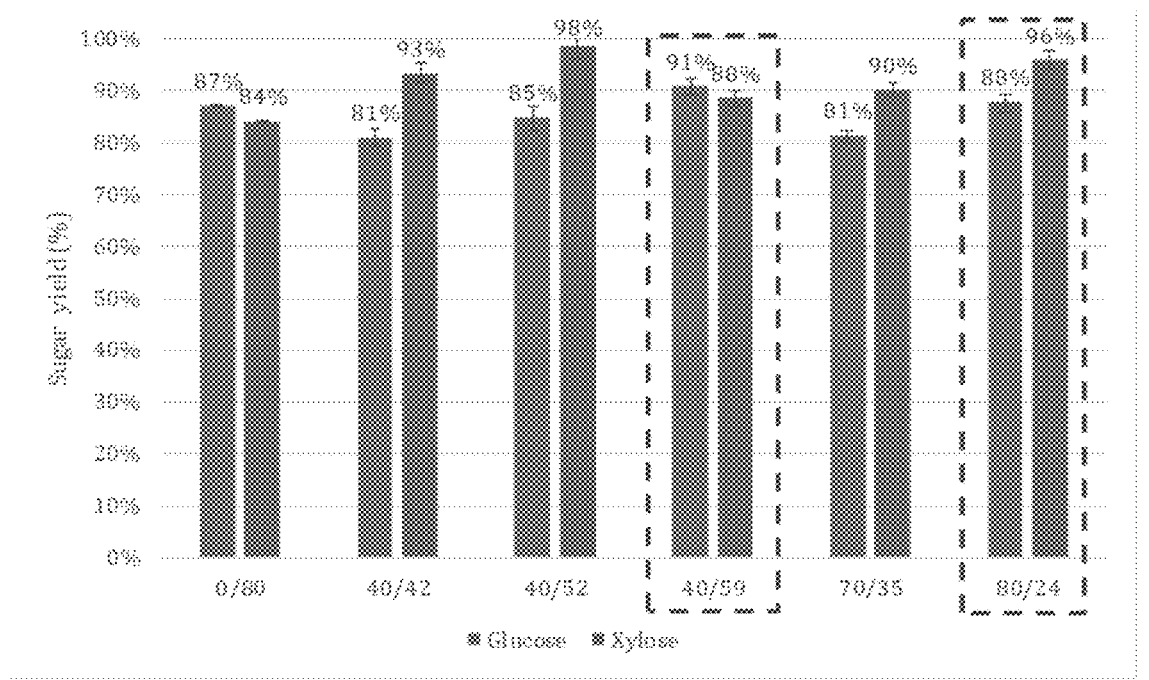
FIG. 4 depicts the effect of two-stage deacetylation severity on enzymatic hydrolysis sugar yields at 10 mg total protein (8 mg of Novozymes CTec3 and 2 mg of HTec3 per gram of cellulose) at 20% solids for 7 days. The numbers on the x-axis are $Na_2CO_3$ and NaOH loadings, with the number before "/" showing $Na_2CO_3$ loading and the number after "/" showing the NaOH loading with both units in kg/tonne, respectively. For example, "40/42" means 40 kg $Na_2CO_3$/tonne of biomass used in $1^{st}$ stage deacetylation and 42 kg NaOH/tonne of biomass used in $2^{nd}$ stage deacetylation, all based on original biomass weight.

FIG. 4 discloses the effects of the control and the two-stage deacetylation on enzymatic hydrolysis sugar yields at 10 mg total protein (8 mg CTec3 and 2 mg of HTec3) per gram of cellulose at 20% solids for 7 days. Increasing solids to 20% does not decrease the sugar yields in many of the cases when compared to the 2% enzymatic hydrolysis experiments. For example, the control sample shows similar sugar yields (87% glucose and 84% xylose) as compared to yields at 2% solids (88% glucose and 84% xylose). The 2-stage deacetylated and mechanical refined biomass also showed similar results. The two cases with 40/59 and 80/24 resulted in superior sugar yields, especially the 40/59 case exceeded our target conversion goals by producing 90% glucose yield and 87% xylose yield at 20% solids during enzymatic hydrolysis. The 80/24 case also showed excellent sugar yields (87% glucose and 94% xylose) at this comparatively low enzyme loading. The xylose yields at 20% solids were higher (in the range of 7-17%) than those yields at 2% solids when using the two-stage DMR corn stover.

Figure 5:
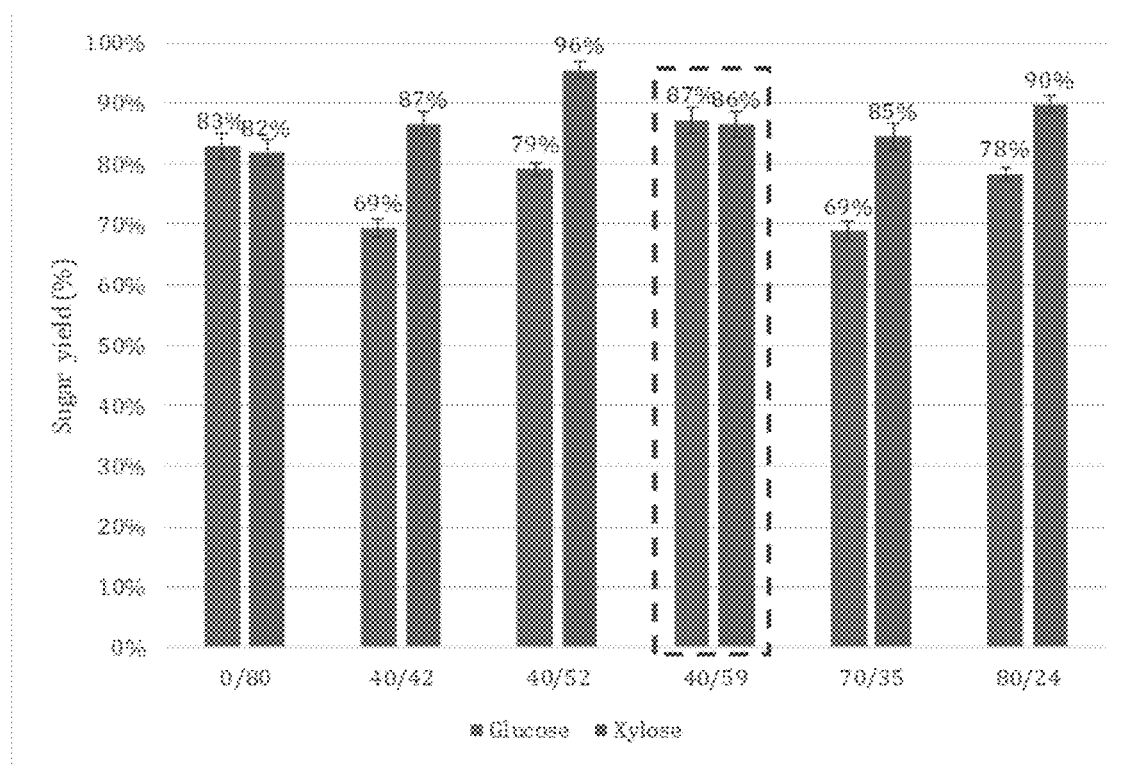
FIG. 5 depicts the effect of two-stage deacetylation severity on enzymatic hydrolysis sugar yields at 8 mg of Novozymes CTec3 and 2 mg of HTec3 per gram of cellulose at 22.5% solids for 7 days. The numbers on the x-axis are $Na_2CO_3$ and NaOH loadings, with the number before "/" showing $Na_2CO_3$ loading and the number after "/" showing the NaOH loading with both units in kg/tonne, respectively. For example, "40/42" means 40 kg $Na_2CO_3$/tonne of biomass used in $1^{st}$ stage deacetylation and 42 kg NaOH/tonne of biomass used in $2^{nd}$ stage deacetylation, all based on original biomass weight.

FIG. 5 shows the effects of the control and the two-stage deacetylation on enzymatic hydrolysis sugar yields at 10 mg total protein (8 mg CTec3 and 2 mg of HTec3 enzymes) per gram of cellulose at 22.5% solids for 7 days. We found that increasing the solids from 20% to 22.5% insoluble solids decreases the sugar yields in multiple cases by 4-13% for glucose and 2-7% for xylose. The low enzyme loadings (10 mg total protein (for example, 8 mg of Novozymes CTec3 and 2 mg of Novozymes HTec3) per gram of cellulose and higher solids significantly extended the liquefaction times of enzymatic hydrolysis from 24-48 hours at 20% solids to 48-72 hours at 22.5% solids and thus reduces the enzyme activities and the final sugar yields. The control sample shows 83% glucose and 82% xylose yield, while the 40/59 case still shows excellent sugar yields with 87% glucose and 86% xylose yield, respectively. Thus, we were able to demonstrate 87% glucose yield and 86% xylose yield at an enzyme loading of 10 mg total protein/g of cellulose at 22.5% solids with reduced (26%) sodium hydroxide usage in deacetylation.

Figure 6A:
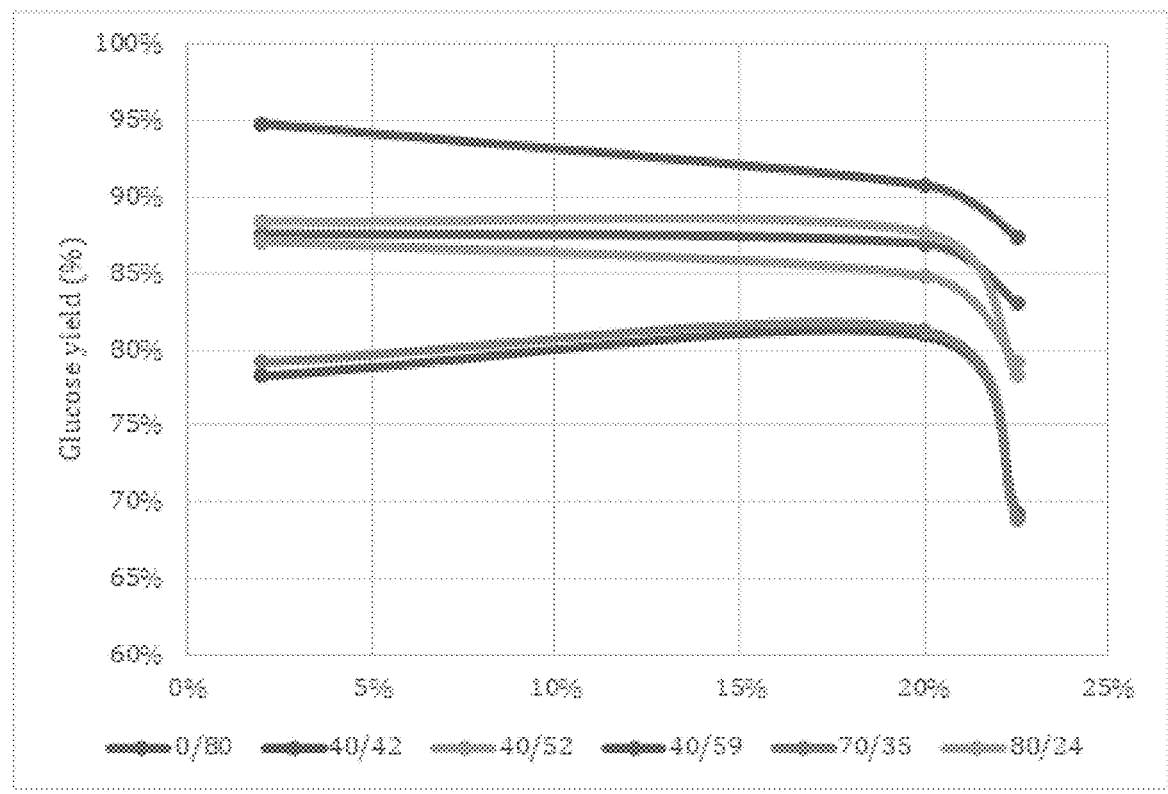
FIG. 6A depicts the effect of initial insoluble solids loadings of biomass in enzymatic hydrolysis on glucose yield.
Figure 6B:
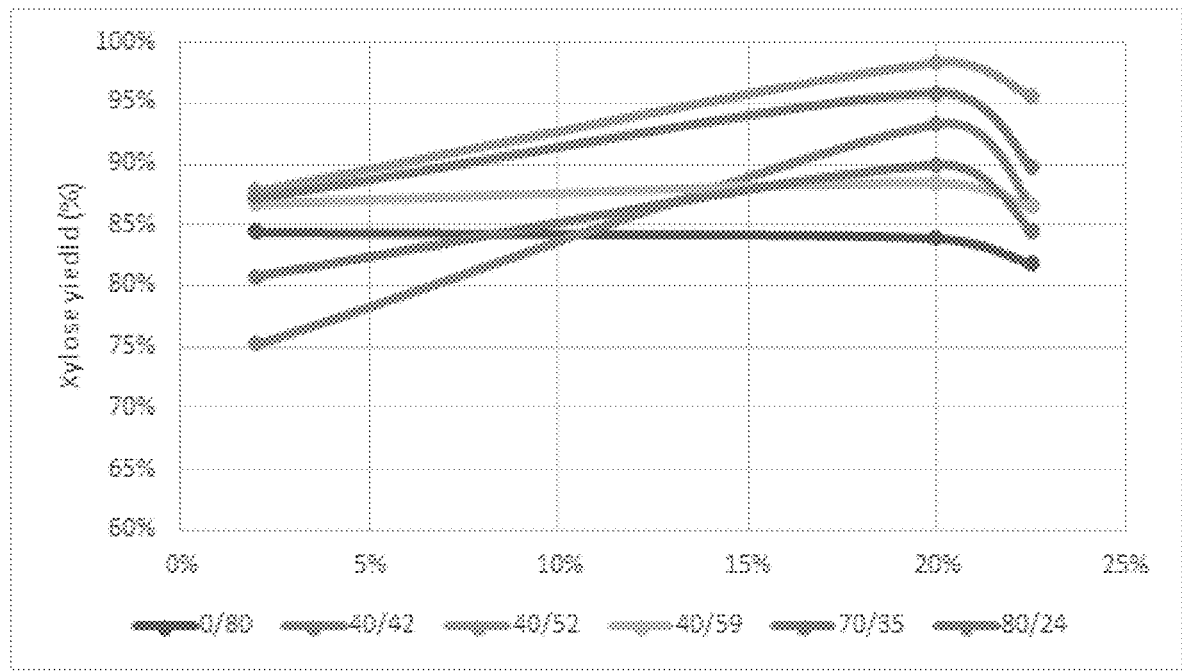
FIG. 6B depicts the effect of initial insoluble solids loadings of biomass in enzymatic hydrolysis on xylose yield.

The above yield data are aggregated for glucose in FIG. 6A and for xylose in FIG. 6B to show the effect of initial insoluble solids loadings of biomass on enzymatic hydrolysis.

iii. GHG Emissions and Chemical Cost Reduction

By using the two-stage deacetylation, we have successfully demonstrated that higher sugar yields can be achieved with lower total GHG emissions. As shown in Table 4, in multiple cases (case 2 and 4), we have reduced GHG emissions and chemical cost by up to 30% with equivalent sugar yields (5% lower glucose yield and 5-13% higher xylose yield). For case 3, we successfully increased sugar yields by 3% for both glucose and xylose yields, with 10% reduction on GHG emissions and 9% on chemical cost, respectively. For case 5, we showed 37% reduction on both GHG and chemical cost with same glucose yield and 10% higher xylose yields.

TABLE 4

Comparison of GHG emissions and chemical cost for single stage NaOH deacetylation and two stage Na$_2$CO$_3$ and NaOH deacetylation. Enzymatic hydrolysis (EH) conducted at 20% solids and 10 mg per g of cellulose.

| Case No. | Na$_2$CO$_3$ loading* | NaOH loading* | Glucose yield vs. control | Xylose yield vs. control | Total GHG emission due to alkali usages (CO$_2$e/kg) | GHG reduction vs. control | Total chemical cost reduction compared to control |
|---|---|---|---|---|---|---|---|
| Control | NA | 80 | 87% | 84% | 168 | NA | NA |
| 1 | 40 | 42 | −6% | +9% | 116.2 | 31% | 31% |
| 2 | 40 | 52 | −2% | +14% | 137.2 | 18% | 18% |
| 3 | 40 | 59 | +4% | +4% | 151.9 | 10% | 9% |
| 4 | 70 | 35 | −6% | +6% | 122.5 | 27% | 27% |
| 5 | 80 | 24 | 1% | +12% | 106.4 | 37% | 37% |

Figure 7:
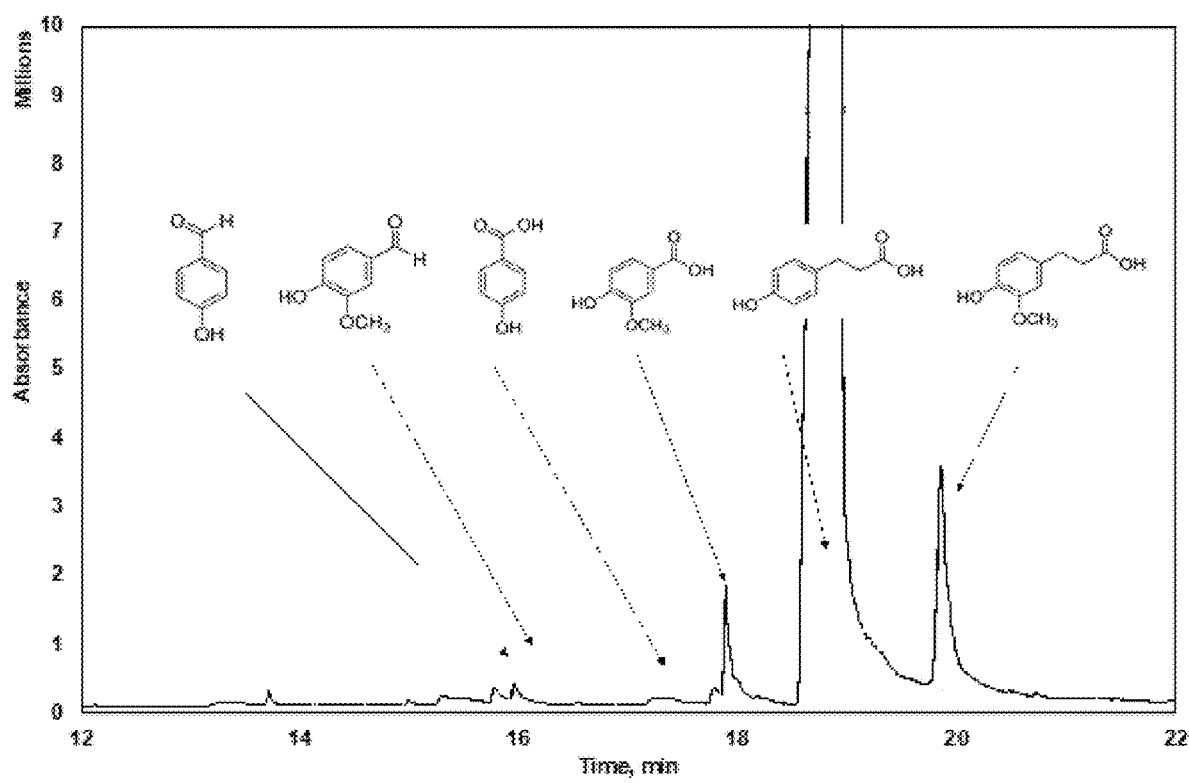
FIG. 7 depicts a representative GC-MS chromatogram of a lignin oil obtained from ethyl acetate extraction of hydrolysate obtained after ozone treatment of lignin isolated from corn stover DMR-EH residual solids.

*Loading in kg/tonne biomass)

iv. Effect of Ozone Treatment on Enzymatic Hydrolysis Yields of the Two-Stage DM Ozone treated DMR corn stover was prepared with and without post washing. Ozonolysis oxidizes the β-carbon in the propyl side chain of lignin and phenolic rings in the lignin structure, making the oxidized products much more soluble. We characterized and quantified six lignin-derived monomeric aromatic compounds from the ozone treated process liquor (shown in FIG. 7).

The solubilized lignin may cause inhibition of enzymes in the enzymatic hydrolysis step. Generally, complete washing of the ozonated DMR biomass would be ideal for downstream processing. However, washing will very likely increase the operational costs due to water and energy usages. Thus, as disclosed herein, we compared the sugar yields using non-washed and partially washed two-stage deacetylation DMR corn stover with ozonolysis.

TABLE 5

The effect of ozone treatment and post washing on enzymatic hydrolysis sugar yields of two-stage deacetylation DMR of corn stover.

| | $Na_2CO_3$ (kg/tonne) | NaOH (kg/tonne) | Ozonolysis (min) | Glucose Yield | Xylose Yield |
|---|---|---|---|---|---|
| Control_1 | 40 | 52 | | 87.1% | 87.8% |
| O1_unwashed | 40 | 52 | 15 | 80.9% | 81.3% |
| O2_washed | 40 | 52 | 15 | 88.4% | 93.0% |
| O1_unwashed | 40 | 52 | 30 | 81.3% | 82.1% |
| O2_washed | 40 | 52 | 30 | 90.8% | 95.5% |
| Control_2 | 40 | 42 | | 78.3% | 75.3% |
| O2_unwashed | 40 | 42 | 15 | 80.0% | 79.2% |
| O2_washed | 40 | 42 | 15 | 93.7% | 98.9% |
| Control_3 | 70 | 32 | | 79.1% | 80.7% |
| O3_unwashed | 70 | 32 | 15 | 77.0% | 77.1% |
| O3_washed | 70 | 32 | 15 | 84.8% | 89.2% |
| Control_4 | 80 | 25 | | 88.3% | 87.3% |
| O4_unwashed | 80 | 25 | 15 | 81.8% | 80.8% |
| O4_washed | 80 | 25 | 15 | 87.0% | 95.9% |
| O4_unwashed | 80 | 25 | 30 | 77.9% | 76.4% |
| O4_washed | 80 | 25 | 30 | 87.0% | 88.5% |

Table 5 shows the effect of ozone treatment and post washing on enzymatic hydrolysis sugar yields at enzyme loading of 8 mg CTec3 and 2 mg of HTec3 per gram of cellulose at 2% solids for 7 days. With partially washing of the biomass (200 g DI water for 50 g of dry biomass, centrifuged for 10 minutes for separation), the washed ozonated DMR corn stover shows higher glucose and xylose yields. For example, the 40/42 (control 2) case showed improved glucose yield by almost 15% to 94% and xylose yield by 24% to 99% after ozonolysis and washing. The 70/32 sample case also increased glucose yield by 6% from 79% to 85% and xylose yield by 9% from 81% to nearly 90%. The 80/25 case does not show a significant glucose yield improvement after ozonolysis and washing as the control sample already achieved nearly 90% glucose yield. But the ozonolysis and washing does help improve the xylose yield by almost 9%.

However, the non-washed ozonated DMR corn stover showed significantly lower sugar yields compared to the control samples. In all the cases, both glucose and xylose yields show lower yields by 10-14% for glucose and 10-20% for xylose yield, suggesting the ozonolysis products are strong inhibitors of enzymatic hydrolysis and should be removed by extensive washing prior to enzymatic hydrolysis.

Figure 8A:
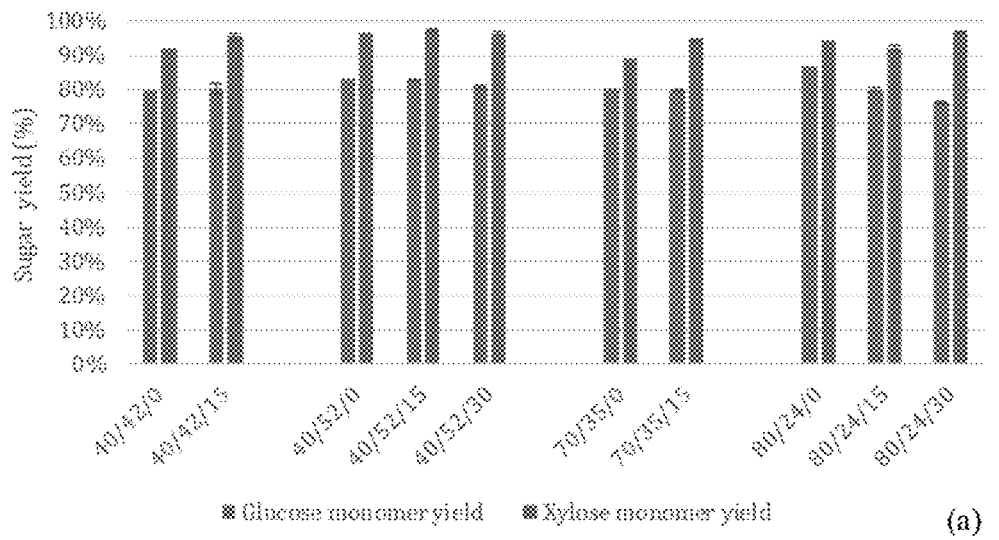
FIG. 8A depicts the effect of two-stage deacetylation severity on enzymatic hydrolysis sugar yields at £10 mg total protein (8 mg Novozymes CTec3 and 2 mg of HTec3) per gram of cellulose at 20% insoluble solids for 7 days. The numbers on the x-axis show $Na_2CO_3$, NaOH loadings, and ozonolysis reaction times. For example, "40/42/15" means 40 kg $Na_2CO_3$/tonne of biomass used in $1^{st}$ stage deacetylation, 42 kg NaOH/tonne of biomass used in $2^{nd}$ stage deacetylation and 15 minutes of ozonolysis, all based on original biomass weight.
Figure 8B:
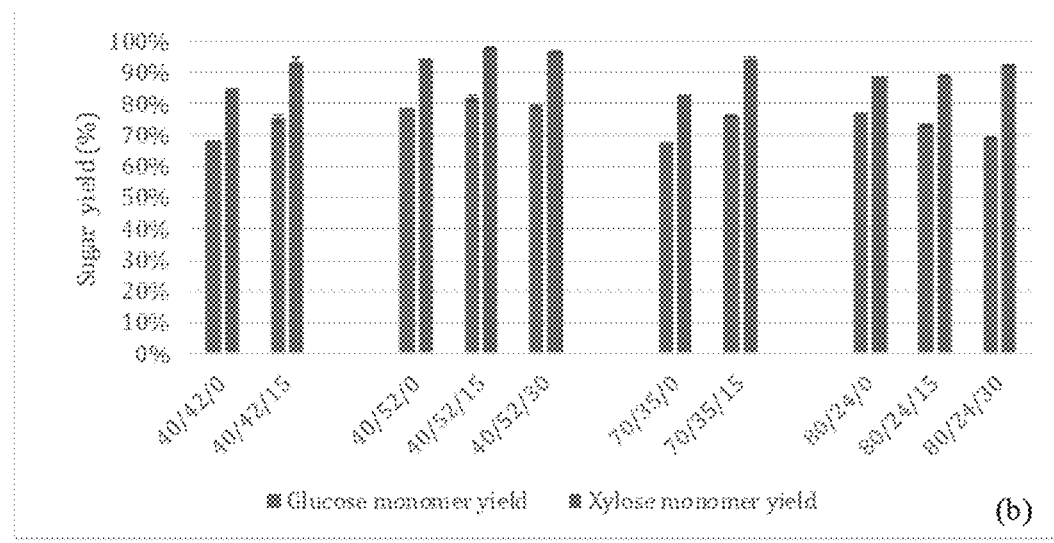
FIG. 8B depicts the effect of two-stage deacetylation severity on enzymatic hydrolysis sugar yields at (10 mg total protein (8 mg Novozymes CTec3 and 2 mg of HTec3) per gram of cellulose at 22.5% insoluble solids for 7 days. The numbers on the x-axis show $Na_2CO_3$, NaOH loadings, and ozonolysis reaction times. For example, "40/42/15" means 40 kg $Na_2CO_3$/tonne of biomass used in $1^{st}$ stage deacetylation, 42 kg NaOH/tonne of biomass used in $2^{nd}$ stage deacetylation and 15 minutes of ozonolysis, all based on original biomass weight.

FIG. 8A and FIG. 8B show the effects of ozonolysis on enzymatic hydrolysis sugar yields with partially washed single- and two-stage deacetylation DMR corn stover at (10 mg total protein=8 mg CTec3 and 2 mg of HTec3) per gram of cellulose at 20% (FIG. 8A) and 22.5% (FIG. 8B) insoluble solids for 7 days. Unlike the yield improvements shown in Table 3, we did not observe an improvement in sugar yields at higher solids. Without being bound by theory, it is possible that the washing is incomplete and at 20 and 22.5% solids the concentration of the inhibitors is much higher than at 2% solids, leading to reduced improvements on sugar yields.

Example 2. Production of Dicyclohexane and Other Value-Added Products from Ozonated Lignin Moieties Conversion and valorization of lignin into value-added products has gained increased attention; however, its efficient utilization has been challenging partly due to the heterogenous structure of lignin. Thus, disclosed herein are catalytic processes for the conversion of DMR lignin to lignin-substructure-based di- or tri-cyclic hydrocarbons ($C_{11}$-$C_{16}$) via depolymerization and oxidation reactions followed by catalytic upgrading via Diels Alder and hydrodeoxygenation (HDO) reactions.

As depicted in Scheme 1, the first step of the process involves oxidation of the monomers and low molecular weight (LMW) fractions produced with ozonated lignin moieties from deacetylation black liquor to a mixture of quinones, e.g., mono-methoxybenzoquionone (MMBQ) and dimethoxybenzoquionone (DMBQ). The MMBQ/DMBQ mixture is then reacted with a diene such as isoprene or biomass derived 1,3-butadiene via Diels Alder reaction to yield di- or tri-cyclic adducts. Finally, hydrodeoxygenation (HDO) of di- or tri-cyclic adducts under mild reaction conditions (250° C.) using noble metal catalysts (e.g., Pt/MCM41) can be conducted to yield di- or tri-cyclic hydrocarbons ($C_{11}$-$C_{16}$) with excellent fuel properties that can be blended with jet fuels.

Scheme 1. Schematic representation for the conversion of DMR derived lignin monomers to lignin-substructure-based di- or tri- cyclic hydrocarbons ($C_{11}$-$C_{16}$).

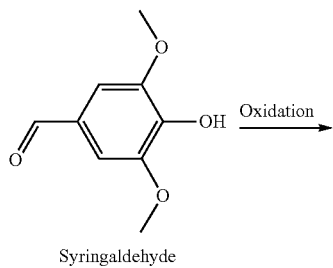

Syringaldehyde

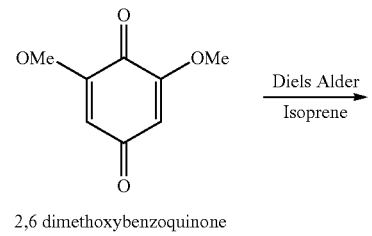

2,6 dimethoxybenzoquinone

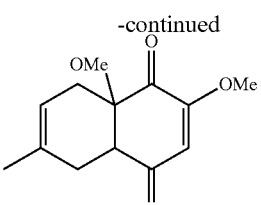

+

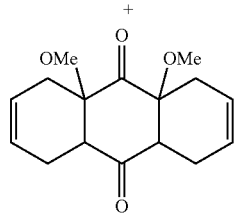

di- or tri cyclic adducts

HDO →

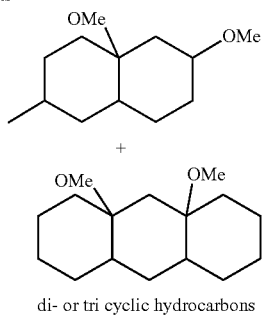

+ di- or tri cyclic hydrocarbons

GC-MS analyses of hydrolysates obtained after ozone treatment of DMR-CS showed six main lignin monomers, 4-hydroxybenzaldehyde, vanillin, 4-hydroxybenzoic acid, vanillic acid, 3-(4-hydroxyphenyl) propionic acid and 3-(4-hydroxy-3-methoxyphenyl) propionic acid. Benzoquinones may be produced via oxidation of lignin monomers. Particularly, 4-hydroxybenzaldehyde, and 4-hydroxybenzoic acid are promising quinone precursors with the oxidation of syringic acid using Fremy's salt producing 2,6-dimethoxybenzoquinone in near 100% yield. Disclosed herein is the Diels Alder conversion of lignin monomer derived quinones to di- or tri-cyclic adducts to find the optimum reaction conditions to produce the adducts. HDO of the adducts to yield di- or tri-cyclic hydrocarbons ($C_{11}$-$C_{16}$) was performed and GC-MS and NMR analyses were used to characterize the resulting products including dicyclohexane molecules.

A. Diels Alder Reaction—Methods and Materials

The reactants (2, 6 DMBQ and isoprene) and Lewis acid catalyst ($AlCl_3 \cdot 6H_2O$ or $SnCl_4 \cdot 5H_2O$) were added to dichloromethane in equimolar amounts at room temperature to give 0.1 M concentration in each. Experiments were conducted in glass vials at moderate stirring. For the analysis of the reactant and products, aliquots (20 μL) were taken from the reaction vial at predetermined time intervals and diluted in dichloromethane 50-fold to terminate the reaction. The samples were analyzed with GC-MS for monitoring and analysis of the products.

B. Diels Alder Conversion of 2,6 Dimethoxybenzoquinone

The oxidation of syringic acid, a monomer that can be obtained by ozone treatment of lignin, using Fremy's salt, produces 2,6 dimethoxybenzoquinone (DMBQ) in 98% yield. Therefore, in this study, DMBQ was used as a model compound representing ozonated lignin monomer to produce adducts. The Diels Alder reaction between DMBQ, 1 and isoprene leads to the formation of more than one adduct depending on how many molecules of isoprene add to DMBQ. As shown in Scheme 2, the addition of one molecule of isoprene to DMBQ will lead to the formation of a monoadduct, 2 and the addition of two molecules of isoprene will form a bisadduct, 3.

Scheme 2. Schematic representation for the conversion of DMR derived lignin monomers to lignin-substructure-based di- or tri- cyclic hydrocarbons ($C_{11}$-$C_{16}$).

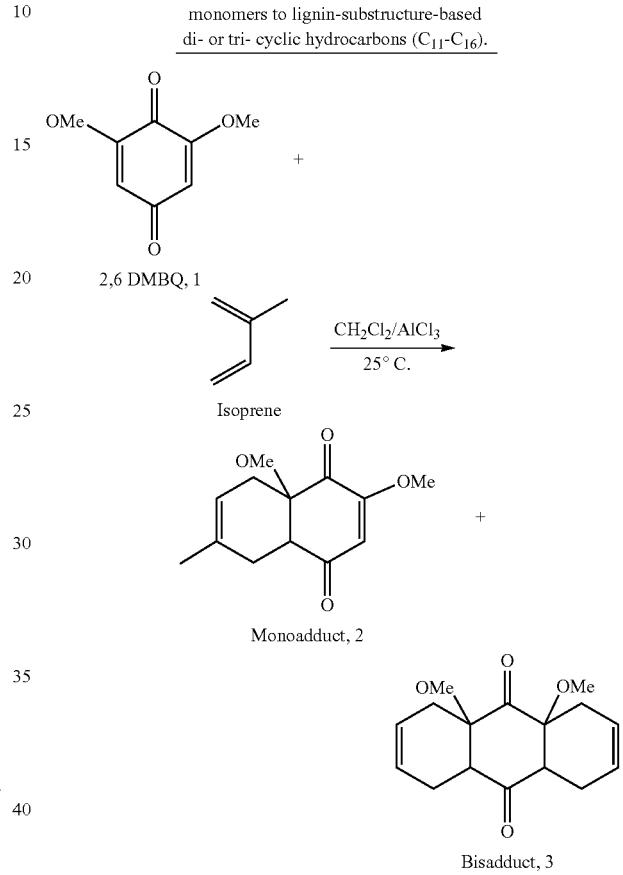

Figure 9:
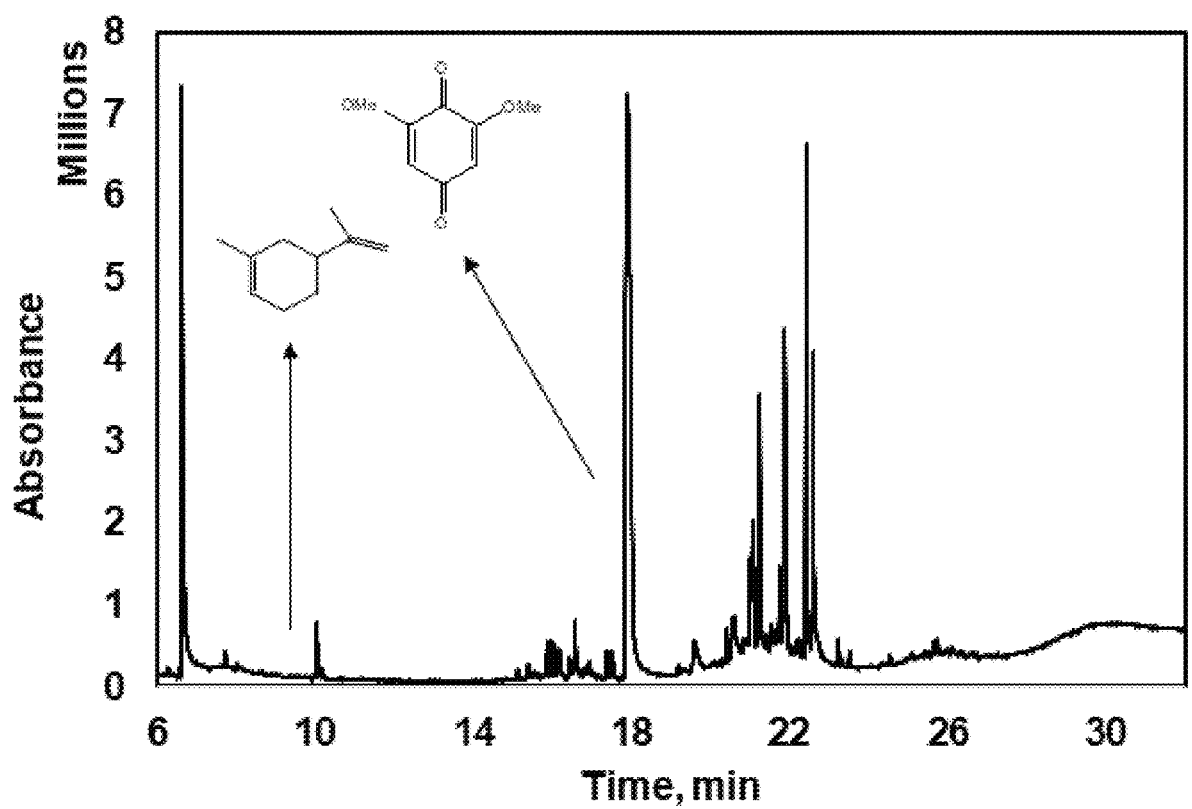
FIG. 9 depicts a representative GC-MS chromatogram of adducts obtained after Diels Alder reaction between 2,6 dimethoxybenzoquinone and isoprene using $BF_3Et_2O$ as a Lewis acid catalyst at 0° C. for a reaction time of 30 min.

In the Diels Alder reaction between quinones and isoprene, the presence of Lewis acids such as boron trifluoride ($BF_3Et_2O$) can produce a significant increase in the rate and yield of the adduct formation. Accordingly, $BF_3Et_2O$ was used a Lewis acid catalyst in our preliminary experiments. The analysis of the reaction products by GCMS are shown in FIG. 9. It shows the residual DMBQ, as well as the formation of various adducts (between the retention time of 20-24 min). Though it was encouraging to see formation of the adducts, the formation of too many adducts suggested that the catalytic action of $BF_3$ is non-selective thereby posing a significant challenge in the isolation, identification and characterization of all the adducts. Further Diels Alder experiments were conducted using aluminum chloride ($AlCl_3$) and stannic chloride ($SnCl_4$) to see if this resulted in the adduct formation with high yields and selectivity.

The GC-MS analysis of the products for the Diels Alder reaction conducted between DMBQ and isoprene using $SnCl_4$ and $AlCl_3$ are depicted in FIG. 11. As depicted in FIG. 11A, the reaction using $SnCl_4$ as a catalyst resulted in a significant improvement in the product selectivity resulting in the production of both mono (MW—204) and bis adducts (MW—236) with the monoadduct being the major adduct formed (retention time, 21.5 min). The GCMS results for the reaction conducted using $AlCl_3$ (FIG. 11B) are very similar to that obtained with $SnCl_4$ except the bis adduct was formed in much smaller quantities. The MW of the monoadduct formed was 204 (instead of 236) which suggests that it is formed via a loss of MeOH from the monoadduct, 2 as shown in Scheme 3. In addition, a peak at 10.0 min also appear which is identified to be the Diels Alder dimer of isoprene.

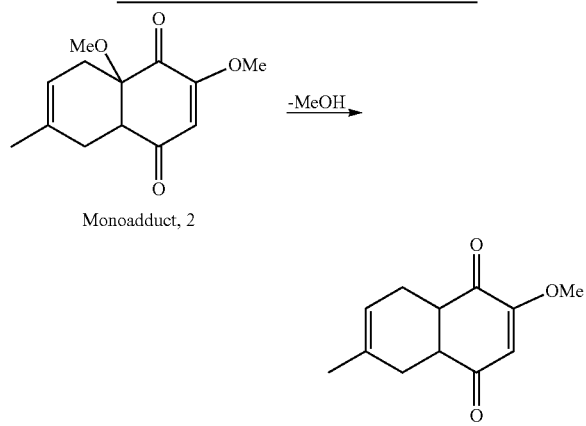

Scheme 3. GC-MS results suggested further reaction of monoadduct resulting in the loss of MeOH and formation of the intermediate with MW = 204, and retention time = 21.5 min.

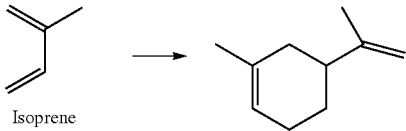

Scheme 4. GCMS results suggested Diels Alder dimer of isoprene, rentention time - 10.0 min.

TABLE 6

The conversion of DMBQ with two different Lewis acid catalysts after Diels Alder reaction with isoprene at 25° C. for 30 min

| | DMBQ conversion, % | Reaction temperature, ° C. | Reaction time, min |
|---|---|---|---|
| $SnCl_4$ | 50.5 | 25 | 30 |
| $AlCl_3$ | 45 | 25 | 30 |

Furthermore, a calibration curve using GCMS was developed for DMBQ to quantify the residual amount of DMBQ still remaining at the end of the reaction period. The conversion yields are reported in Table 6. The results depict that about 50% conversion of DMBQ was achieved in a reaction time of 30 min at 25° C. with slightly higher conversions were achieved with $SnCl_4$. These results have clearly demonstrated that mono and bis adducts can be produced from DMBQ via Diels Alder reaction at room temperature in 30 min reaction time. Therefore, the Diels Alder reaction conditions are amenable to optimization to increase the conversion of DMBQ and isolate the adducts for their quantification as well as their conversion to dicyclohexane molecules via HDO under mild conditions (250° C.) using noble metal catalysts (Pt/MCM 41).

The implementation of a two-stage deacetylation strategy using $Na_2CO_3$ in the first stage as an option to the DMR process allows for equivalent or higher enzymatic hydrolysis yields when compared to a standard single-stage NaOH deacetylation DMR process. This process option reduces chemical costs by substituting a lower cost alkali ($Na_2CO_3$) that allows lower usage of the higher cost NaOH. In addition, the use of $Na_2CO_3$ lowers the greenhouse gas (GHG) costs associated with the DMR process, thus making the lower cost alkali much more favorable.

Using methods and compositions disclosed herein, the lignin solubilized in the deacetylation steps can be upgraded to mono- and di-cyclohexane products suitable for high energy density jet fuel blend stocks to increase aircraft payloads and range.

Lignin content of biomass shows complicated impacts on biomass digestibility. From previous research, high lignin content could be detrimental to enzymatic hydrolysis due to unproductive binding of the enzymes and thus result in lower sugar yields. From the 2-stage deacetylation and ozonolysis pretreatment, it was discovered that over delignification of biomass can also lead to lower sugar yields. Without being limited by theory, the extensive removal of lignin from biomass could potentially destroy the porous structure of biomass and reduce the enzyme accessibility. Thus, as disclosed herein, a "sweet spot" of lignin content does exist for biomass, especially for corn stover, to achieve high sugar yields at low enzyme loadings.

Without being limited by theory, thorough washing of ozonated biomass to remove the lignin oxidative products could be very important for subsequent enzymatic hydrolysis. The unwashed ozonated biomass showed significantly lower sugar yields compared to washed biomass, suggesting the inhibition of the oxidative products from ozonolysis.

The foregoing disclosure has been set forth merely to illustrate the invention and is not intended to be limiting.

What is claimed is:

1. A method for treating lignocellulosic biomass for ethanol production, comprising:
    (i) reacting the lignocellulosic biomass with a first alkali to produce a first stage biomass;
    (ii) dewatering the first stage biomass to isolate a first stream of first stage solids;
    (iii) reacting the first stage solids with a second alkali to produce a second stage biomass;
    (iv) dewatering the second stage biomass to isolate a stream of second stage solids; and
    (v) mechanically refining the second stage solids, comprising the use of at least one of a single disk mill, a double disk mill, a conical plate mill, a pin mill, a ball mill, a Szego type mill, an attrition mill, an ultrasonics-assisted mill, a stone-wheel grinding mill, or a homogenizer,
    wherein the first alkali has a pH of from about 10 to about 12, and the second alkali has a pH of 12 or greater, and
    wherein the lignocellulosic biomass comprises a hemicellulose, and wherein less than 4% of the hemicellulose is solubilized in step (i).

2. The method of claim 1, further comprising:
    (vi) dewatering the mechanically refined second stage solids;
    (vii) isolating the solids from step (vi), wherein the solids comprise cellulose; and (viii) enzymatically hydrolyzing the isolated solids from step (vii).

3. The method of claim 1, wherein the first alkali is selected from at least one of sodium carbonate, potassium carbonate, ammonium hydroxide, magnesium hydroxide, trimethylamine, or methylamine.

4. The method of claim 1, wherein the second alkali is selected from at least one of sodium hydroxide, potassium hydroxide, barium hydroxide, calcium hydroxide, trisodium phosphate, or tripotassium phosphate.

5. The method of claim 1, further comprising an additional mechanical refining step after the mechanical refining of the second stage solids of step (v).

6. The method of claim 2, wherein enzymatically hydrolyzing the isolated solids from step (vii) uses about 10 to about 50 mg of plant cell wall hydrolytic and oxidative enzymes per gram of cellulose in the isolated solids from step (vii).

7. The method of claim 2, further comprising isolating sugars from the enzymatically hydrolyzed isolated solids from step (viii), wherein the sugars are isolated at greater than about an 80% yield.

8. The method of claim 1, wherein an amount of lignin in the lignocellulosic biomass is reduced by about 5% to about 15% by steps (i) and (ii), and reduced by about 20% to about 40% by steps (iii) and (iv).

\* \* \* \* \*